(12) United States Patent
Haung

(10) Patent No.: US 6,500,920 B1
(45) Date of Patent: Dec. 31, 2002

(54) INHIBITOR OF TRANSFORMING GROWTH FACTOR β AND A METHOD OF INHIBITING THE BIOLOGICAL EFFECTS OF TRANSFORMING GROWTH FACTOR

(75) Inventor: Jung San Haung, St.Louis, MO (US)

(73) Assignee: St. Louis University, St. Louis, MO (US)

( * ) Notice: Subject to any disclaimer, the term of this patent is extended or adjusted under 35 U.S.C. 154(b) by 0 days.

(21) Appl. No.: 09/095,637

(22) Filed: Jun. 11, 1998

Related U.S. Application Data

(60) Provisional application No. 60/050,202, filed on Jun. 19, 1997.

(51) Int. Cl.$^7$ .......................... C07K 7/06; C07K 7/08; C07K 14/00; C07K 14/495; C12N 5/06
(52) U.S. Cl. ...................... 530/328; 530/324; 530/325; 530/326; 530/327; 435/325
(58) Field of Search ................................. 530/324, 328, 530/327, 326, 329, 325; 435/325

(56) References Cited

U.S. PATENT DOCUMENTS 5,444,151 A * 8/1995 Vassbotn et al. ............. 530/324

FOREIGN PATENT DOCUMENTS

EP 0 433 225 A1 * 6/1991

OTHER PUBLICATIONS

Postlethwaite et al. Identification of a chemotactic epitope in human transforming growth factor–beta 1 spanning amino acid residues 368–374. J Cell Physiol. Sep. 1995;164(3):587–92.*

Rudinger, J. "Characteristics of the amino acids as components of a peptide hormone sequence", in, Peptie Hormones, University Park Press, Jun. 1976.*

Bowie et al. Deciphering the message in protein sequences: tolerance to amino acid substitutions. Science, (Mar. 16, 1990) 247 (4948) 1306–10.*

Ngo et al., in The Protein Folding Problem and Tertiary Structure Prediction, Merz and Le Grand (Eds), Aug. 1994, Springer Verlag, pp. 433 and 492–495.*

Shah et al. J. Cell Sci., (Mar. 1995) 108 (Pt 3) 985–1002.*

Qian et al. Identification of a structural domain that distinguishes the actions of the type 1 and 2 isoforms of transforming growth factor beta on endothelial cells. Proc Natl Acad Sci U S A. Jul. 1992 15;89(14):6290–4.*

Miller et al. GenBank Database Accession No. M32745. National Center for Biotechnology Information, Bethesda, MD. Apr. 27, 1993.*

Kingsley DM. The TGF–beta superfamily: new members, new receptors, and new genetic tests of function in different organisms. Genes Dev. Jan. 1994;8(2):133–46.*

McDonald et al. A structural superfamily of growth factors containing a cystine knot motif. Cell. May 1993 7;73(3):421–4.*

Mittl et al. The crystal structure of TGF–beta 3 and comparison to TGF–beta 2: implications for receptor binding. Protein Science, (Jul. 1996) 5 (7) 1261–71.*

Derynck et al., Human transforming growth factor–β complementary DNA sequence and expression in normal and transformed cells, Nature 316:701–705 (1985).

Hinck et al., Transforming Growth Factor β1: Three–Dimensional Structure in Solution and Comparison with the X–ray Structure of Transforming Growth Factor β2, Biochemistry 35:8517–8534 (1996).

Huang et al., Transforming Growth Factor β Peptide Antagonists and Their Conversion to Partial Agonists, J. Biol. Chem. 272:27155–27159 (1997).

Huang et al., Activated Thyroglobulin Possesses a Transforming Growth Factor–βActivity, J. Biol. Chem. 273:26036–26041 (1998).

Huang et al., A Pentacosapeptide (CKS–25) Homologous to Retroviral Envelope Proteins Possesses a Transforming Growth Factor–β Activity, J. Biol. Chem. 273:4815–4818 (1998).

Huang et al., Amyloid β–Peptide Possesses a Transforming Growth Factor–β Activity,J. Biol. Chem. 273:27640–17644 (1998).

Huang et al., An Active Site of Transforming Growth Factor–$β_1$ for Growth Inhibition and Stimulation, J. Biol. Chem. 274:27754–27758 (1999).

Laiho et al., Concomitant Loss of Transforming Growth Factor (TGF)– β Receptor Types I and II in TGF–β–resistant Cell Mutants Implicates Both Receptor Types in Signal Transduction, J. Biol. Chem. 265:18518–18524 (1990).

Liu et al., Function of the Type V Transforming Growth Factor β Receptor in Transforming Growth Factor β–induced Growth Inhibition of Mink Lung Epithelial Cells, J. Biol. Chem. 272:18891–18895 (1997).

Madisen et al., Transforming Growth Factor–β2: cDNA Cloning and Sequence Analysis, DNA 7:1–8 (1988).

O'Grady et al., Purification of a New Type High Molecular Weight Receptor (Type V Receptor) of Transforming Growth Factor β (TGF–β) from Bovine Liver,J. Biol. Chem. 266:8583–8589 (1991).

Schlunegger et al., An ususual feature revealed by the crystal structure at 2.2Å resolution of human transforming growth factor–β2, Nature 358:430–434 (1992).

* cited by examiner

Primary Examiner—David S. Romeo

(57) ABSTRACT

A method of inhibiting, ameliorating or reversing the effects of TGF-β in biological systems by exposing the bioligical systems with an agent which substantially represents active site peptide of the TGF-β molecules.

36 Claims, 5 Drawing Sheets

|  | 1 | 25 |
|---|---|---|
| Human TGF-β₁ | A L D T N Y C F S S T E K N C C V R Q L Y I D F R | |
| Human TGF-β₂ | A L D A A Y C F R N V Q D N C C L R P L Y I D F K | |
| Human TGF-β₃ | A L D T N Y C F R N L E E N C C V R P L Y I D F R | |

|  | 26 | 50 |
|---|---|---|
| Human TGF-β₁ | K D L G W K W I H E P K G Y H A N F C L G P C P Y | |
| Human TGF-β₂ | R D L G W K W I H E P K G Y N A N F C A G A C P Y | |
| Human TGF-β₃ | Q D L G W K W V H E P K G Y Y A N F C S G P C P Y | |

|  | 51 | 75 |
|---|---|---|
| Human TGF-β₁ | I W S L D T Q Y S K V L A L Y N Q H N P G A S A A | |
| Human TGF-β₂ | L W S S D T Q H S R V L S L Y N T I N P E A S A S | |
| Human TGF-β₃ | L R S A D T T H S T V L G L Y N T L N P E A S A S | |

|  | 76 | 100 |
|---|---|---|
| Human TGF-β₁ | P C C V P Q A L E P L P I V Y Y V G R K P K V E Q | |
| Human TGF-β₂ | P C C V S Q D L E P L T I L Y Y I G K T P K I E Q | |
| Human TGF-β₃ | P C C V P Q D L E P L T I L Y Y V G R T P K V E Q | |

|  | 101 | 112 |
|---|---|---|
| Human TGF-β₁ | L S N M I V R S C K C S | |
| Human TGF-β₂ | L S N M I V K S C K C S | |
| Human TGF-β₃ | L S N M V V K S C K C S | |

Fig. 5 (A)

|  | 41 | 65 |
|---|---|---|
| β₁²⁵41-65 | A N F C L G P C P Y I W S L D T Q Y S K V L A L Y | |
| β₂²⁵41-65 | A N F C A G A C P Y L W S S D T Q H S R V L S L Y | |
| β₃²⁵41-65 | A N F C S G P C P Y L R S A D T T H S T V L G L Y | |

SEQUENCE LISTING

<160> NUMBER OF SEQ ID NOS: 11

<210> SEQ ID NO 1
<211> LENGTH: 112
<212> TYPE: PRT
<213> ORGANISM: Homo sapiens

<400> SEQUENCE: 1

```
Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Pro Cys Cys Val Pro
 65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 2
<211> LENGTH: 112
<212> TYPE: PRT
<213> ORGANISM: Homo sapiens

<400> SEQUENCE: 2

```
Ala Leu Asp Ala Ala Tyr Cys Phe Arg Asn Val Gln Asp Asn Cys Cys
 1               5                  10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
 65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 3
<211> LENGTH: 112
<212> TYPE: PRT
<213> ORGANISM: Homo sapiens

<400> SEQUENCE: 3

```
Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45
```

```
Pro Tyr Leu Arg Ser Ala Asp Thr Thr His Ser Thr Val Leu Gly Leu
         50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
            100                 105                 110

<210> SEQ ID NO 4
<211> LENGTH: 25
<212> TYPE: PRT
<213> ORGANISM: Homo sapiens

<400> SEQUENCE: 4

Ala Asn Phe Cys Leu Gly Pro Cys Pro Tyr Ile Trp Ser Leu Asp Thr
 1               5                  10                  15

Gln Tyr Ser Lys Val Leu Ala Leu Tyr
             20                  25

<210> SEQ ID NO 5
<211> LENGTH: 25
<212> TYPE: PRT
<213> ORGANISM: Human

<400> SEQUENCE: 5

Ala Asn Phe Cys Ala Gly Ala Cys Pro Tyr Leu Trp Ser Ser Asp Thr
 1               5                  10                  15

Gln His Ser Arg Val Leu Ser Leu Tyr
             20                  25

<210> SEQ ID NO 6
<211> LENGTH: 25
<212> TYPE: PRT
<213> ORGANISM: Homo sapiens

<400> SEQUENCE: 6

Ala Asn Phe Cys Ser Gly Pro Cys Pro Tyr Leu Arg Ser Ala Asp Thr
 1               5                  10                  15

Thr His Ser Thr Val Leu Gly Leu Tyr
             20                  25

<210> SEQ ID NO 7
<211> LENGTH: 10
<212> TYPE: PRT
<213> ORGANISM: Homo sapiens

<400> SEQUENCE: 7

Pro Tyr Ile Trp Ser Leu Asp Thr Gln Tyr
 1               5                  10

<210> SEQ ID NO 8
<211> LENGTH: 10
<212> TYPE: PRT
<213> ORGANISM: Homo sapiens

<400> SEQUENCE: 8

Pro Tyr Leu Trp Ser Ser Asp Thr Gln His
 1               5                  10

<210> SEQ ID NO 9
<211> LENGTH: 10
```

```
<212> TYPE: PRT
<213> ORGANISM: Homo sapiens

<400> SEQUENCE: 9

Pro Tyr Leu Arg Ser Ala Asp Thr Thr His
 1               5                   10

<210> SEQ ID NO 10
<211> LENGTH: 4
<212> TYPE: PRT
<213> ORGANISM: Homo sapiens
<220> FEATURE:
<221> NAME/KEY: PEPTIDE
<222> LOCATION: (1)..(4)
<223> OTHER INFORMATION: Residue 3 is any amino acid

<400> SEQUENCE: 10

Trp Ser Xaa Asp
 1

<210> SEQ ID NO 11
<211> LENGTH: 4
<212> TYPE: PRT
<213> ORGANISM: Homo sapiens
<220> FEATURE:
<221> NAME/KEY: PEPTIDE
<222> LOCATION: (1)..(4)
<223> OTHER INFORMATION: Residue 3 is any amino acid

<400> SEQUENCE: 11

Arg Ser Xaa Asp
 1
```

INHIBITOR OF TRANSFORMING GROWTH FACTOR β AND A METHOD OF INHIBITING THE BIOLOGICAL EFFECTS OF TRANSFORMING GROWTH FACTOR

CROSS REFERENCE TO RELATED APPLICATION

This application claims priority from an earlier filed provisional patent application Ser. No. 60/050,202, filed Jun. 19, 1997.

ACKNOWLEDGMENT

This invention was made with the US Government support awarded by the National Institutes of Health. The US Government may have certain rights in the invention.

BACKGROUND OF THE INVENTION

Transforming growth factor β (TGF-β) is a family of 25-kDa structurally homologous dimeric proteins containing one interchain disulfide bond and four intrachain disulfide bonds. The TGF-β family is composed of three-known members (TGF-$β_1$, TGF-$β_2$, and TGF-$β_3$) in mammalian species. TGF-β is a bifunctional growth regulator: it is a growth inhibitor for epithelial cells, endothelial cells, T-cells, and other cell types and a mitogen for mesenchymal cells. TGF-β also has other biological activities, including stimulation of collagen, fibronectin, and plasminogen activator inhibitor 1 (PAI-1) synthesis, stimulation of angiogenesis, and induction of differentiation in several cell lineages.

TGF-β has been implicated in the pathogenesis of various diseases such as intimal hyperplasia following angioplasty, tissue fibrosis, and glomerulonephritis. Neutralizing antibodies to TGF-β have been used experimentally to reduce scarring of wounds, to prevent lung injury in adult respiratory distress syndrome (ARDS), and to block restenosis following angioplasty in animal models. These promising results warrant the development of TGF-β antagonists (inhibitor) that might be useful in inhibiting, ameliorating or reversing the effects of TGF-β and treating diseases.

SUMMARY OF THE INVENTION

A method of inhibiting, ameliorating or reversing the effects of TGF-β in biological systems, comprising the step of exposing said biological systems with a binding agent, said binding agent is a peptide which substantially resembles a segment of the TGF-β molecules.

The binding agent is a peptide which substantially resembles an active site of the TGF-β molecules, hereinafter referred to as active site peptide.

The binding agent may be in the form of a peptide or other chemical agents which substantially resembles an active site of the TGF-β molecule, the binding agents occupy the TGF-β cellular receptors making the TGF-β cellular receptors unavailable for the binding of TGF-β molecules.

The biological systems may be either in-vitro or in-vivo.

Most preferably, the binding agent of TGF-β substantially corresponds to a peptide having an amino acid sequence substantially extending from residue 41 to residue 65 of TGF-β amino acid sequence. Most preferably, said binding agents correspond to an amino acid sequence motif preferably represented by WSXD (SEQ ID NO:10) and/or RSXD (SEQ ID NO:11), wherein X represents any amino acid.

Yet another object of the present invention is to provide an active site of TGF-β molecules. And to provide an amino acid sequence which substantially represents an active site of TGF-β molecules.

Yet another object of the present invention is to provide an agonist of TGF-β molecules, comprising a carrier molecule have a plurality of said binding agent. Furthermore, a method of producing an agonist of TGF-β molecules, comprising the step of conjugating a plurality of said binding agents to a carrier molecule.

BRIEF DESCRIPTION OF THE DRAWINGS

Cells were incubated with $^{125}$I-TGF-$β_1$ (Panels A and D), $^{125}$I-TGF-$β_2$ (Panel B), and $^{125}$I-TGF-$β_3$ (Panel C) both with and without 100-fold excess of unlabeled TGF-β isoforms and various concentrations of $β_1^{25}$ (41–65)(SEQ ID NO:4), $β_2^{25}$ (41–65)(SEQ ID NO:5), and $β_3^{25}$ (41–65)(SEQ ID NO:6)(Panels A, B, and C) or of $β_1^{10}$ (49–58)(SEQ ID NO:7), $β_2^{10}$ (49–58)(SEQ ID NO:8), $β_3^{10}$ (49–58)(SEQ ID NO:9), $β_1^{10}$ (49–58) W52A, $β_2^{10}$ (49–58) S53A, $β_2^{10}$ (49–58) D55A, $β_1^{25}$ (41–65) W52A/D55A and $β_3^{25}$ (41–65) R52A/D55A (Panel D). The specific binding of $^{125}$I-labeled TGF-β isoforms was then determined. The specific binding obtained in the absence of peptide antagonists was taken as 0% inhibition. The specific binding (0% inhibition) of $^{125}$I-TGF-$β_1$, $^{125}$I-TGF-$β_2$, and $^{125}$I-TGF-$β_3$ were 3930+540 cpm/well, 4512±135 cpm/well and 4219±125 cpm/well, respectively. The error bars are means ± of triplicate cultures.

Cells were incubated with $^{125}$I-TGF-$β_1$ in the presence of 100-fold excess of unlabeled TGF-$β_1$ (lane 1) and of various concentrations of $β_1^{25}$ (41–65) (lanes 8-13) and $β_3^{25}$ (41–65) (lanes 2–7). The $^{125}$I-TGF-$β_1$-affinity labeling was carried out in the presence of DSS. The $^{125}$I-TGF-$β_1$ affinity-labeled TGF-β receptors were analyzed by 5% SDS-polyacrylamide gel electrophoresis and autoradiography. The arrow indicates the location of the $^{125}$I-TGF-$β_1$ affinity-labeled type V TGF-β receptor (TβR-V). The brackets indicate the locations of the $^{125}$I-TGF-$β_1$ affinity-labeled type I, type II, and type III TGF-β receptors (TβR-I, TβR-II, and TβR-III).

Figure 3:
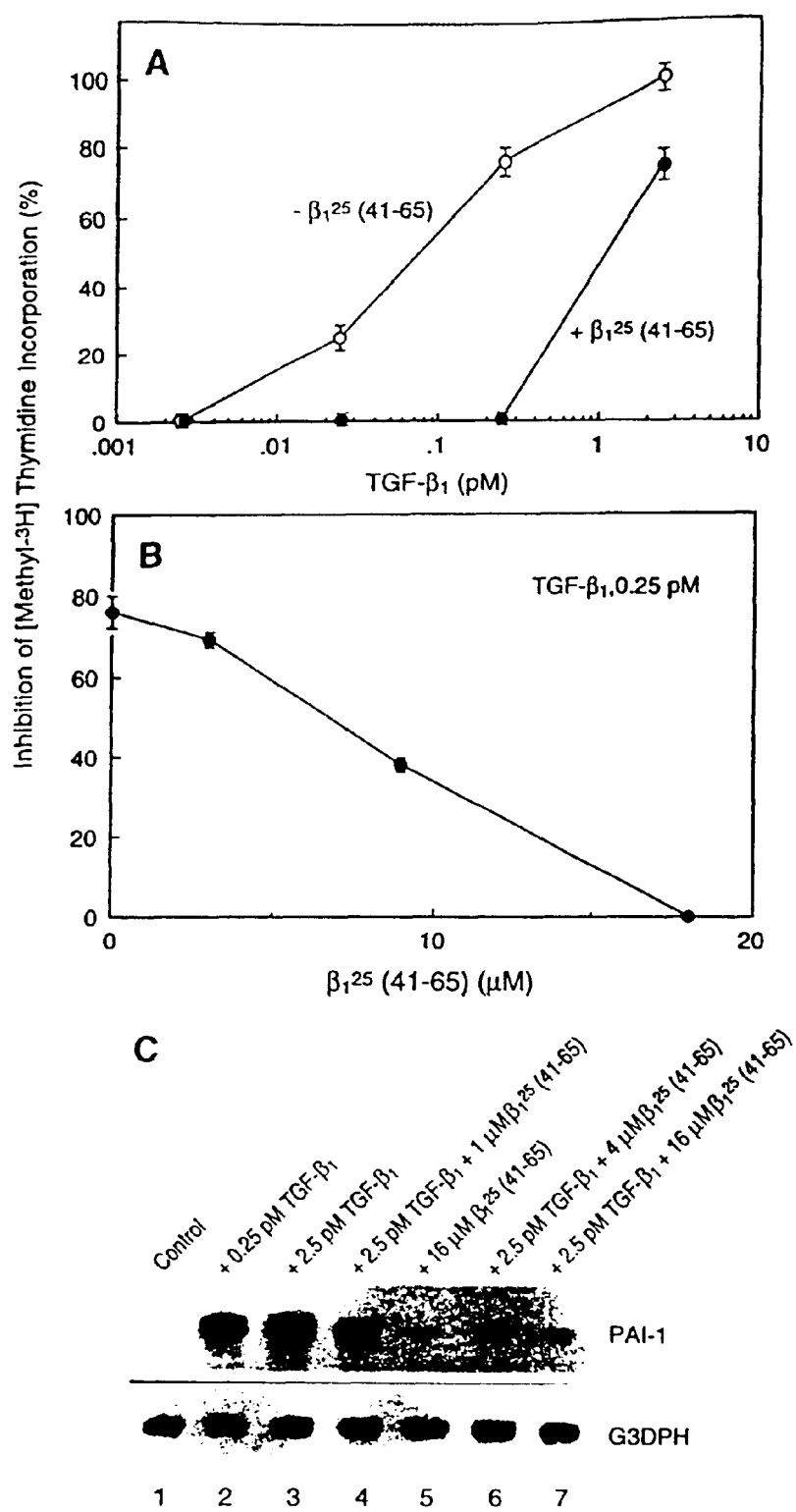

FIG. 3. Effect of $β_1^{25}$ (41–65) on TGF-$β_1$-induced growth inhibition as measured by DNA synthesis (Panels A and B) and TGF-$β_1$-induced PAI-1 expression (Panel C) in mink lung epithelial cells.

(Panel A) Cells were incubated with various concentrations of TGF-$β_1$ in the presence of 18 μM $β_1^{25}$ (41–65). [Methyl-$^3$H]thymidine incorporation into cellular DNA was then determined. The [methyl-$^3$H]thymidine incorporation into cellular DNA in cells treated with and without 10 pM TGF-$β_1$ were taken as 100 and 0% inhibition. The error bars are means± S.D. of triplicate cultures. (Panel B) Cells were incubated with 0.25 pM TGF-β, in the presence of various concentrations of $β_1^{25}$ (41–65). The [methyl-$^3$H]thymidine incorporation into cellular DNA in cells treated with and without 10 pM TGF-$β_1$ were taken as 100 and 0% inhibition, respectively. The error bars are means± S.D. of triplicate cultures. (Panel C) Cells were treated with 0.25 and 2.5 pM TGF-$β_1$ and various concentrations of $β_1^{25}$ (41–65) for 3 hr. The transcriptional expressions of PAI-1 and glyceraldehyde-3-phosphate dehydrogenase (G3PDH) were determined by Northern blot analysis.

Figure 4:
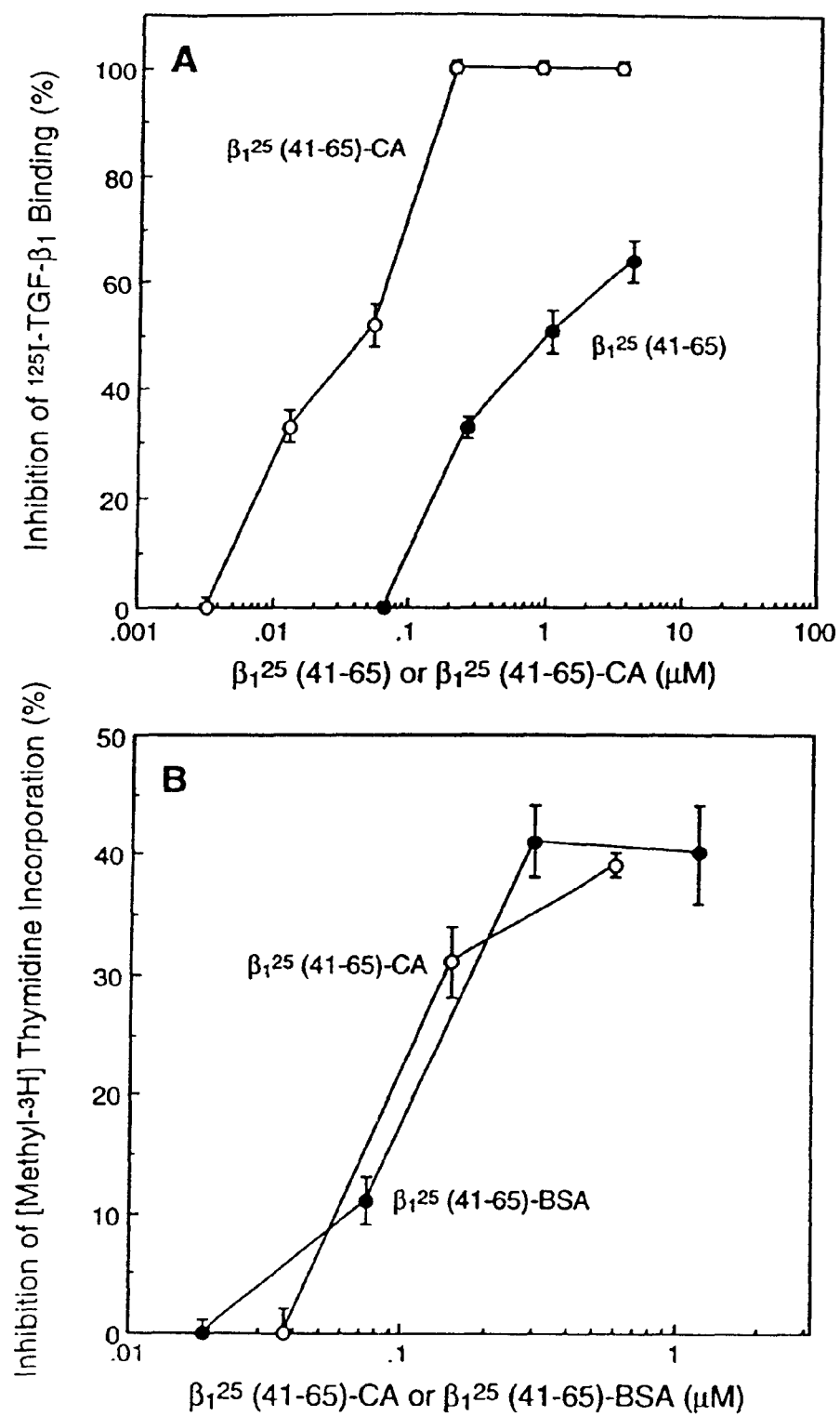

FIG. 4. Effect of $\beta_1{}^{25}$ (41–65)-CA and $\beta_1{}^{25}$ (41–65)-BSA conjugates on $^{125}$I-TGF-$\beta_1$ binding to TGF-$\beta$ receptors in mink lung epithelial cells (Panel A) and on mink lung epithelial cell growth as measured by DNA synthesis (Panel B).

(Panel A) Cells were incubated with $^{125}$I-TGF-$\beta_1$ in the presence and absence of 100-fold excess of unlabeled TGF-$\beta_1$ and various concentrations of $\beta_1{}^{25}$ (41–65)-CA conjugate. The specific binding of $^{125}$I-TGF-$\beta_1$ was then determined. The specific binding of $^{125}$I-TGF-$\beta_1$ obtained in the absence of the conjugates was taken as 0% inhibition. The error bars are means± S.D. of triplicate cultures. (Panel B) Cells were treated with various concentrations of $\beta_1{}^{25}$ (41–65)-CA or $\beta_1{}^{25}$ (41–65)-BSA conjugate. [Methyl-$^3$H] thymidine incorporation into cellular DNA was determined. The [methyl-$^3$H]thymidine incorporation into cellular DNA in cell treated with and without 10 pM TGF-$\beta_1$ were taken as 100 and 0% inhibition, respectively. The error bars are means± S.D. of triplicate cultures.

FIG. 5A shows the amino acid sequence of human TGF-$\beta_1$ (SEQ ID NO:1), human TGF-$\beta_2$ (SEQ ID NO:2), and human TGF-$\beta_3$ (SEQ ID NO:3); FIG. 5B shows the amino acid sequence of $\beta_1{}^{25}$(41–65)(SEQ ID NO:4), $\beta_2{}^{25}$(41–65) (SEQ ID NO:5), and $\beta_3{}^{25}$(41–25)(SEQ ID NO:6), which consist of amino acids 41–65 of TGF-$\beta_1$, TGF-$\beta_2$, and TGF-$\beta_3$, respectively.

DESCRIPTION OF THE INVENTION

The object of the invention is to develop TGF-$\beta$ antagonists or inhibitors with specificities toward the type V TGF-$\beta$ receptor and other TGF-$\beta$ receptor types (type I, type II, and type III receptors). It was discovered that three chemically synthesized pentacosapeptides (i.e. binding agents), $\beta_1{}^{25}$ (41–65), $\beta_2{}^{25}$ (41–65), and $\beta_3{}^{25}$ (41–65), whose amino acid sequences were derived from and correspond to the 41st to 65th amino acid residues of TGF-$\beta_1$, TGF-$\beta_2$, and TGF-$\beta_3$, inhibit the binding of radiolabeled TGF-$\beta_1$, TGF-$\beta_2$, and TGF-$\beta_3$ to TGF-$\beta$ receptors in mink lung epithelial cells (i.e. cellular receptors). It was also discovered that the W/RXXD motif in the sequences determines their potencies and that they block TGF-$\beta$-induced growth inhibition and TGF-$\beta$-induced expression of PAI-1 in mink lung epithelial cells. It was also discovered that these TGF-$\beta$ peptide antagonists can be converted to partial agonists (i.e. agent which mimics the effects of TGF-$\beta$) by conjugation to carriers such as proteins or synthetic polymers.

To develop synthetic peptide antagonists of TGF-$\beta$, seven pentacosapeptides were synthesized $\beta_1{}^{25}$ (21–45), $\beta_1{}^{25}$ (41–65), $\beta_1{}^{25}$ (51–75), $\beta_1{}^{25}$ (61–85), $\beta_1{}^{25}$ (71–95), and $\beta_1{}^{25}$ (81–105), whose amino acid sequences overlap one another and cover most of the human TGF-$\beta_1$ molecule, the monomer of which has 112 amino acid residues (1). The antagonist activities of these peptides were first tested for their abilities to inhibit $^{125}$I-labeled TGF-$\beta_1$ ($^{125}$I-TGF-$\beta_1$) binding to cell-surface TGF-$\beta$ receptors in mink lung epithelial cells, a standard model system for investigating TGF-$\beta$ receptor types and TGF-$\beta$-induced cellular responses (2). $\beta_1{}^{25}$ (41–65), whose amino acid sequence corresponds to the 41st-65th amino acid residues of TGF-$\beta_1$, completely inhibited the $^{125}$I-TGF-$\beta_1$ binding (specific binding without peptides=3672±524 cpm/well) to TGF-$\beta$ receptors in mink lung epithelial cells at 34 $\mu$M. The other six pentacosapeptides did not show any effect on $^{125}$I-TGF-$\beta_1$ binding to TGF-$\beta$ receptors in these epithelial cells even at a concentration of 136 $\mu$M. This suggests that $\beta_1{}^{25}$ (41–65) is a TGF-$\beta$ inhibitor or antagonist and contain an active-site amino acid sequence of TGF-$\beta_1$.

Figure 1:
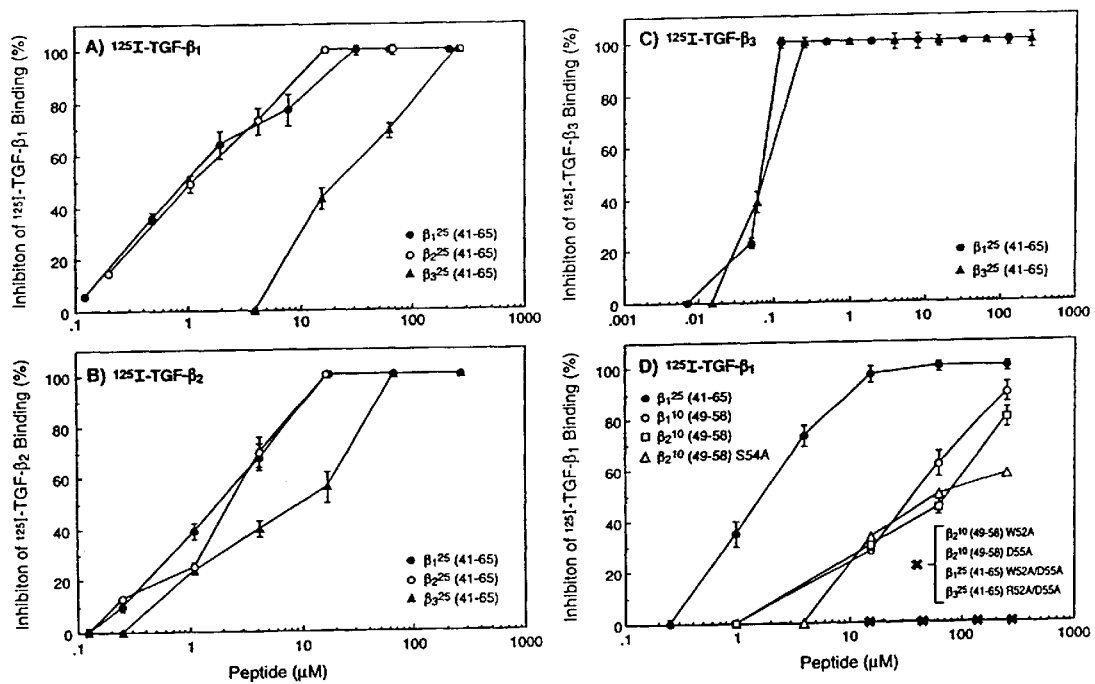
FIG. 1. Effect of various concentrations of pentacosapeptides, decapeptides, and their structural variants on $^{125}$I-TGF-$β_1$, (Panels A and D), $^{125}$I-TGF-$β_2$ (Panel B), and $^{125}$I-TGF-$β_3$ (Panel C) binding to TGF-β receptors in mink lung epithelial cells.

TGF-$\beta$ isoforms (TGF-$\beta_1$, TGF-$\beta_2$, and TGF-$\beta_3$) have been shown to exhibit different potencies in inducing cellular responses in certain cell types or systems. There is 70% amino acid sequence homology at the 41st to 65th amino acid residues among these three TGF-$\beta$ isoforms (1–3). To determine the potencies of $\beta_1{}^{25}$ (41–65), $\beta_2{}^{25}$ (41–65), and $\beta_3{}^{25}$ (41–65) in terms of TGF-$\beta$ antagonist activity, applicant measured the effects of these peptides on the binding of $^{125}$I-labeled TGF-$\beta_1$, TGF-$\beta_2$, and TGF-$\beta_3$ to TGF-$\beta$ receptors in mink lung epithelial cells. As shown in FIG. 1, both $\beta_1{}^{25}$ (41–65) and $\beta_2{}^{25}$ (41–65) inhibited $^{125}$I-TGF-$\beta_1$ and $^{125}$I-TGF-$\beta_2$ binding to TGF-$\beta$ receptors in a concentration-dependent manner with an $IC_{50}$ of ~1–2 $\mu$M (FIG. 1, A and B). $\beta_3{}^{25}$ (41–65) was weaker with an $IC_{50}$ of ~20 $\mu$M for inhibiting $^{125}$I-TGF-$\beta_1$ and $^{125}$I-TGF-$\beta_2$ binding to TGF-$\beta$ receptors (FIG. 1A and B). In contrast, $\beta_1{}^{25}$ (41–65) and $\beta_3{}^{25}$ (41–65) showed equal potency ($IC_{50}$=~0.06–0.08 $\mu$M) when $^{125}$I-TGF-$\beta_3$ was used as ligand for testing the inhibitory activity (FIG. 1C). $\beta_2{}^{25}$ (41–65) also had an $IC_{50}$ of ~0.08 $\mu$M for inhibiting $^{125}$I-TGF-$\beta_3$ binding to TGF-$\beta$ receptors in these epithelial cells (data not shown). These results show that both $\beta_1{}^{25}$ (41–65) and $\beta_2{}^{25}$ (41–65) are more potent antagonists than $\beta_3{}^{25}$ (41–65) for $^{125}$I-TGF-$\beta_1$ and $^{125}$I-TGF-$\beta_2$, and that all three pentacosapeptides are potent antagonists for $^{125}$I-TGF-$\beta_3$ with equal $IC_{50}$.

The region spanning residues 41–65 includes a loop in the three-dimensional structures of TGF-$\beta_1$ and TGF-$\beta_2$ (4,5). This loop is accessible to solvent according to X-ray and NMR analyses (4,5). There are two reasons why a WSXD (for TGF-$\beta_1$ and TGF-$\beta_2$) or RSXD (for TGF-$\beta_3$) motif in the loop is a good candidate site whereby these pentacosapeptides and their parent molecules could interact with TGF-$\beta$ receptors. The W/RSXD (52nd–55th amino acid residues) motif is located on the exposed surface of the loop, and the side chains of the amino acid residues in the motif orient toward the solvent (4,5). Also, this motif may determine the affinities of $\beta_1{}^{25}$ (41–65), $\beta_2{}^{25}$ (41–65), and $\beta_3{}^{25}$ (41–65), and their parent molecules for binding to TGF-$\beta$ receptors. Both $\beta_1{}^{25}$ (41–65) and $\beta_2{}^{25}$ (41–65) share the same motif (WSXD) and have equal potencies ($IC_{50}$=1–2 $\mu$M) for the inhibition of $^{125}$I-TGF-$\beta_1$ binding to TGF-$\beta$ receptors. $\beta_3{}^{25}$ (41–65) possesses a distinct motif of RSXD and is a weaker inhibitor ($IC_{50}$ of 20 EM). The Kds for TGF-$\beta_1$ and TGF-$\beta_2$ binding to the type V TGF-$\beta$ receptor are identical (~0.4 nM), whereas the Kd of TGF-$\beta_3$ binding to the type V receptor is higher (~5 nM) (6). To test the possibility that the W/RSXD motif is the active site of these peptides, applicant synthesized three decapeptides designated $\beta_1{}^{10}$ (49–58), $\beta_2{}^{10}$ (49–58), and $\beta_1{}^{10}$ (49–58) whose amino acid sequences correspond to the 49th–58th amino acid residues of TGF-$\beta_1$, TGF-$\beta_2$, and TGF-$\beta_3$, respectively. The W/RSXD variants of these decapeptides in which the W-52, S-53, or D-55 residue was replaced by an alanine residue were also synthesized and designated $\beta_2{}^{10}$ (49–58) W52A, $\beta_2{}^{10}$ (49–58) S53A, and $\beta_2{}^{10}$ (49–58) D55A, respectively. The abilities of these decapeptides to inhibit $^{125}$I-TGF-$\beta_1$ binding to TGF-$\beta$ receptors in mink lung epithelial cells were then examined. As shown in FIG. 1D, both $\beta_1{}^{10}$ (49–58) and $\beta_2{}^{10}$ (49–58) inhibited the $^{125}$I-TGF-$\beta_1$ binding to TGF-$\beta$ receptors in a concentration-dependent manner with an $IC_{50}$ of ~40–70 $\mu$M. $\beta_3{}^{31}$ (49–58) did not show any inhibitory activity at concentrations up to 300 $\mu$M. $\beta_2{}^{10}$ (49–58) S53A was equipotent with an $IC_{50}$ of 40 $\mu$M. The other variants, $\beta_2{}^{10}$ (49–58) W52A and $\beta_2{}^{10}$ (49–58) D55A, failed to inhibit $^{125}$I-TGF-$\beta_1$ binding to TGF-$\beta$ receptors in these epithelial cells. Identical experiments with $\beta_1^{10}$ (49–58) W52A, $\beta_1^{10}$ (49–58) S53A, and $\beta_1^{10}$ (49–58) D55A were also carried out, and the results were similar to those shown in FIG. 2D with the $\beta_2^{10}$ (49–58) variants (data not shown). These results suggest that the WXXD motif is important for the inhibitory activity of the decapeptides $\beta_1^{10}$ (49–58) and $\beta_2^{10}$ (49–58). To prove that the W/RXXD motif is also important for the inhibitory activities of the pentacosapeptides $\beta_1^{25}$ (41–65) and $B_3^{25}$ (41–65), applicant prepared variants of $\beta_1^{25}$ (41–65) and $\beta_3^{25}$ (41–65), in which both W- or R-52 and D-55 were replaced by alanine residues. These were designated $\beta_1^{25}$ (41–65) W52A/D55A and $\beta_3^{25}$ (41–65) R52A/D55A, respectively, and tested for their inhibitory activities. FIG. 1D shows that $\beta_1^{25}$ (41–65) W52A/D55A and $\beta_3^{25}$ (41–65) R52A/D55A did not inhibit $^{125}$I-TGF-$\beta_1$ binding to TGF-$\beta$ receptors. These results support that the motif W/RXXD is involved in the interactions of the peptide antagonists eith TGF-$\beta$ receptors.

Figure 2:
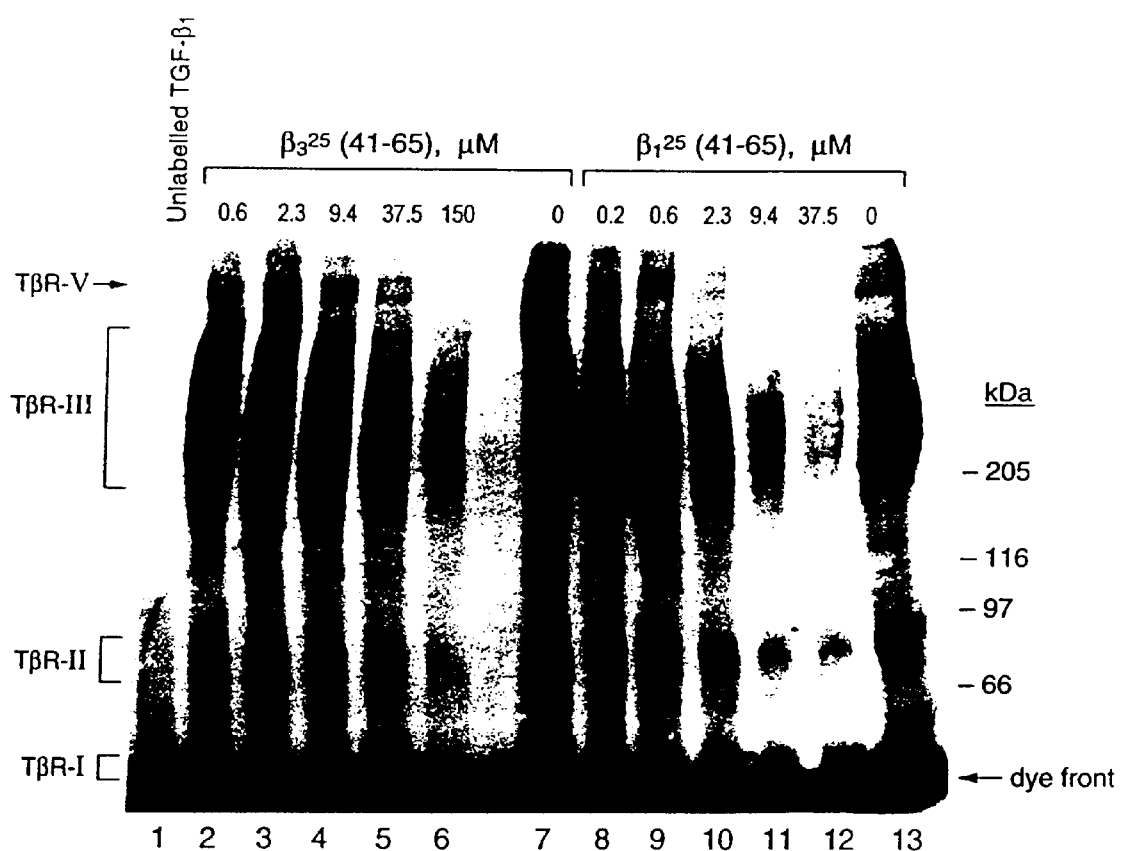
FIG. 2. $^{125}$I-TGF-$β_1$-affinity labeling of cell-surface TGF-β receptors after incubation of mink lung epithelial cells with $^{125}$I-TGF-$β_1$ in the presence of various concentrations of $β_1^{25}$ (41–65) and $β_3^{25}$ (41–65).

Mink lung epithelial cells express all known and well-characterized TGF-$\beta$ receptors (type I, type II, type III, and type V receptors) (6). To determine the relative sensitivities of TGF-$\beta$ receptor types to inhibition by $\beta_1^{25}$ (41–65) and $\beta_3^{25}$ (41–65) with respect to ligand binding, applicant performed $^{125}$I-TGF-$\beta_1$-affinity labeling of cell-surface TGF-$\beta$ receptors after incubation of mink lung epithelial cells with $^{125}$I-TGF-$\beta_1$ in the presence of various concentrations of $\beta_1^{25}$ (41–65) and $\beta_3^{25}$ (41–65). As shown in FIG. 2, all cell-surface TGF-$\beta$ receptors (type I, type II, type III, and type V receptors) were affinity-labeled with $^{125}$I-TGF-$\beta_1$ in the absence of the antagonists (lanes 7 and 13). $\beta_1^{25}$ (41–65) appeared to inhibit the $^{125}$I-TGF-$\beta_1$-affinity labeling of all TGF-$\beta$ receptor types in a concentration-dependent manner (lanes 8–12). However, $B_1^{25}$ (41–65) inhibition of the $^{125}$I-TGF-$\beta_1$-affinity labeling of the type V TGF-$\beta$ receptor was greater than its inhibition of other TGF-$\beta$ receptor types. The $^{125}$I-TGF-$\beta_1$-affinity labeling of the type V TGF-$\beta$ receptor was almost completely abolished by $\beta_1^{25}$ (41–65) at 2.3 $\mu$M, whereas the $^{125}$I-TGF-$\beta_1$-affinity labeling of other TGF-$\beta$ receptor types was only partially inhibited (30–40%) (FIG. 2, lane 10). This result is consistent with applicant's observation that the affinity for TGF-$\beta_1$ binding to the type V TGF-$\beta$ receptor is ~20–40-fold lower than those for TGF-$\beta_1$ binding to other TGF-$\beta$ receptor types (6). $\beta_3^{25}$ (41–65) showed a weak activity in blocking the $^{125}$I-TGF-$\beta_1$-affinity labeling of the type V TGF-$\beta$ receptor (FIG. 2, lanes 2–5).

It has been demonstrated that $\beta_1^{25}$ (41–65), $\beta_2^{25}$ (41–65), and $\beta_3^{25}$ (41–65) are potent inhibitors for $^{125}$I-TGF-$\beta_1$ binding to TGF-$\beta$ receptors. To fulfill the criteria for TGF-$\beta$ antagonists or inhibitor, these pentacosapeptides have to be shown to block TGF-$\beta$-induced cellular responses. One prominent biological activity of TGF-$\beta$ is growth inhibition. Applicant investigated the effect of $\beta_1^{25}$ (41–65) on TGF-$\beta_1$-induced growth inhibition by exposing mink lung epithelial cells to various concentrations of TGF-$\beta_1$ in the presence of 18 $\mu$M $\beta_1^{25}$ (41–65) and measuring cellular DNA synthesis. As shown in FIG. 3A, DNA synthesis inhibition induced by 0.025 and 0.25 pM TGF-$\beta_1$ was completely blocked by $\beta_1^{25}$ (41–55). In the presence of $\beta_1^{25}$ (41–65), the dose-response curve of TGF-$\beta_1$ shifted to the right. $\beta_1^{25}$ (41–65) blocked TGF-$\beta_1$-induced growth inhibition in a concentration-dependent manner (FIG. 3B). It is important to note that $\beta_1^{25}$ (41–65) (0.1 to 36 $\mu$M) did not have an effect on DNA synthesis in the absence of TGF-$\beta_1$. These results suggest that $\beta_1^{25}$ (41–65) is a TGF-$\beta$ antagonist which blocks TGF-$\beta$-induced growth inhibition. The other prominent biological activity of TGF-$\beta$ is transcriptional activation of collagen, fibronectin, and PAI- 1. To see if $\beta_1^{25}$ (41–65) is able to block this activity, applicant investigated the effect of $\beta_1^{25}$ (41–65) on PAI-1 expression in mink lung epithelial cells stimulated by 0.25 and 2.5 pM TGF-$\beta_1$. As shown in FIG. 3C, $\beta_1^{25}$ (41–65) completely blocked the PAI-1 expression stimulated by TGF-$\beta_1$ (lane 7 versus lanes 3 and 5). These results further support that $\beta_1^{25}$ (41–65) is a potent TGF-$\beta$ antagonist.

The dimeric structure of TGF-$\beta$ has been shown to be required for its biological activities. The hetero-oligomerization of TGF-$\beta$ receptors induced by the TGF-$\beta$ dimer appears to trigger signaling. If $\beta_1^{25}$ (41–65) contains the active site sequence involved in the interaction of TGF-$\beta_1$ with TGF-$\beta$ receptors, one may be able to convert its antagonist activity to agonist activity by conjugating $\beta_1^{25}$ (41–65) to carrier proteins, such that the $\beta_1^{25}$ (41–65)-protein conjugates would carry multiple valences of the putative active site. To test this possibility, $\beta_1^{25}$ (41–65) was conjugated to carrier proteins CA (carbonic anhydrase) and BSA (bovine serum albumin) using the cross-linking agent DSS. DSS mainly cross-links the $\alpha$-amino group of $\beta_1^{25}$ (41–65) to the $\epsilon$-amino groups of the carrier proteins. The $\beta_1^{25}$ (41–65)-BSA and $\beta_1^{25}$ (41–65)-CA conjugates contained ~5–10 molecules of $\beta_1^{25}$ (41–65) per molecule of carrier protein. As shown in FIG. 4A, the $\beta_1^{25}$ (41–65)-CA conjugate inhibited $^{125}$I-TGF-$\beta_1$ binding to TGF-$\beta$ receptors in mink lung epithelial cells with an IC$_{50}$ of ~0.05 $\mu$M. The $\beta_1^{25}$ (41–65)-BSA conjugate had a similar IC$_{50}$ of ~0.06 $\mu$M (data not shown). These IC$_{50}$ are ~20-fold lower than that of $\beta_1^{25}$ (41–65) prior to conjugation. In the control experiments, both BSA and CA conjugated without peptides did not have inhibitory activity. These results suggest that the multiple valences of the active site in the protein conjugates enhance its affinity for binding to TGF-$\beta$ receptors. Potential agonist activities of the $\beta_1^{25}$ (41–65)-protein conjugates was also examined. As shown in FIG. 4B, both $\beta_1^{25}$ (41–65)-CA and $\beta_1^{25}$ (41–65)-BSA conjugates induced a small but significant growth inhibition as measured by DNA synthesis with an ED$_{50}$ of 0.1 $\mu$M, although neither showed significant effects on the expression of PAI-1 in mink lung epithelial cells (data not shown). The growth inhibition (30–40%) induced by 0.2 $\mu$M $\beta_1^{25}$ (41–65)-CA could be abolished in the presence of 10 $\mu$M $\beta_1^{25}$ (41–65) (data not shown). These results suggest that these $\beta_1^{25}$ (41–65)-protein conjugates are partial TGF-$\beta$ agonists.

Applicant shows that the W/RXXD motif is a primary site involved in the interaction with TGF-$\beta$ receptors. This is supported by several lines of evidence including: 1) among seven pentacosapeptides whose amino acid sequences cover most of the TGF-$\beta_1$ molecule, only $\beta_1^{25}$ (41–65), which contains the W/RXXD motif in the middle of the peptide amino acid sequence, has TGF-$\beta$ antagonist activity; 2) pentacosapeptides and decapeptides containing this W/RXXD motif are potent TGF-$\beta$ antagonists; 3) replacement of W-52/R-52 and D-55 by alanine residues abolishes the antagonist activities of these decapeptides and pentacosapeptides; 4) conjugation of the $\beta_1^{25}$ (41–65) antagonist to carrier proteins creates a partial TGF-$\beta$ agonist; 5) several proteins that possess W/RXXD motifs have TGF-$\beta$ agonist and antagonist activities.

Most of the experiments in this study were performed using mink lung epithelial cells. However, the antagonist activities of the pentacosapeptides (i.e. binding agents or active site peptides) have been substantially reproduced using a human line i.e. human lung fibroblasts (data not shown). Since TGF-$\beta$ is highly conserved across the species, this invention disclosed herein is substantially valid across species.

Experimental Procedures

Material $Na^{125}I$ (17 Ci/mg) and [methyl-$^3$H]thymidine (67 Ci/mmole) were purchased from ICN Radiochemicals (Irvine, Calif.). High molecular-weight protein standards (myosin, 205 kDa; β-galactosidase, 116 kDa; phosphorylase, 97 kDa; bovine serum albumin, 66 kDa), chloramine T, bovine serum albumin (BSA), and human carbonic anhydrase I (CA) were purchased from Sigma Company (St. Louis, Mo.). Disuccinimidyl suberate (DSS) was obtained from Pierce (Rockford, IL). TGF-$β_1$ was purchased from Austral Biologicals (San Ramon, Calif.). TGF-$β_2$ and TGF-$β_3$ were purchased from R&D Systems (Minneapolis, Minn.).

Preparation of Pentacosapeptides and Decapeptides.

The amino acid sequences of all pentacosapeptides and decapeptides were derived from those of TGF-$β_1$, TGF-$β_2$, and TGF-$β_3$. For pentacosapeptides $β_1^{25}$ (41–65), $β_2^{25}$ (41–65), and $β_3^{25}$ (41–65), other versions in which cysteine-44 and cysteine-48 were replaced by serine residues were also synthesized. These C44S/C48S versions of $β_1^{25}$ (41–65) and $β_2^{25}$ (41–65), and $β_3^{25}$ (41–65) had the same TGF-β antagonist activity. The C44S/C48S versions had better stability in solution during storage, so they were used in most of the experiments. The peptides were synthesized using tert-butoxycarbonyl chemistry on an Applied Biosystems Model 431A peptide synthesizer and purified using Sephadex G-25 column chromatography and reverse-phase HPLC (C-8 column). The purity of the synthesized peptides were verified by automated Edman degradation on an Applied Biosystems Model 477A gas/liquid phase protein sequenator with an on-line Applied Biosystems Model 120A phenylthiohydantoin amino acid analyzer. The purity of all peptides was estimated to be ≧95%.

Preparation of $β_1^{25}$ (41–65)-Carbonic Anhydrase (CA) and $β_1^{25}$ (41–65)-Bovine Serum Albumin (BSA) Conjugates One hundred fifty μl of 3 mM $β_1^{25}$ (41–65) in phosphate buffer saline (pH adjusted to 9.0) was mixed with 300 μl of 0.1 M NaHCO$_3$ (pH ~9.0) containing BSA or CA (0.5 mg) and 10 μl of 27 mM DSS in dimethyl sulfoxide. After 18 hr at 4° C., the reaction mixture was mixed with 50 μl of 1 M ethanolamine HCl in 0.1 M NaHCO$_3$ (~pH 9.0). After 2 hr at room temperature, the reaction mixture was dialyzed against 2 liters of 0.1 M NaHCO$_3$ (pH 9.0). After four changes of the dialysis solution, the sample was stored at 4° C. prior to use. The molar ratio of $β_1^{25}$ (41–65)/carrier protein in the conjugate was determined by amino acid composition analysis.

Specific Binding of $^{125}$I-labeled TGF-$β_1$, TGF-$β_2$, and TGF-$β_3$ ($^{125}$I-TGF-$β_1$, $^{125}$I-TGF-$β_2$, and $^{125}$I-TGF-$β_3$) to TGF-β Receptors in Mink Lung Epithelial Cells $^{125}$I-TGF-$β_1$, $^{125}$I-TGF-$β_2$, and $^{125}$I-TGF-$β_3$ were prepared by iodination of TGF-$β_1$, TGF-$β_2$, and TGF-$β_3$ with $Na^{125}I$ as described previously (7). The specific radioactivities of $^{125}$I-TGF-$β_1$, $^{125}$I-TGF-$β_2$, and $^{125}$I-TGF-$β_3$ were 1–3×10$^5$ cpm/ng. Mink lung epithelial cells were grown on 24-well clustered dishes to near confluence in Dulbecco's modified Eagle medium (DMEM) containing 10% fetal calf serum. The epithelial cells were incubated with 0.1 nM $^{125}$I-TGF-$β_1$, $^{125}$I-TGF-$β_2$, or $^{125}$I-TGF-$β_3$ both with and without 100-fold excess of unlabeled TGF-$β_1$, TGF-$β_2$, or TGF-$β_3$ in binding buffer (7). After 2.5 hr at 0° C., the cells were washed two times with binding buffer, and the cell-associated radioactivity was determined. The specific binding of $^{125}$I-labeled TGF-β isoforms to TGF-β receptors in the cells was calculated by subtracting non-specific binding (in the presence of 100-fold excess of the unlabeled TGF-β isoforms) from total binding. All experiments were carried out in triplicate cell cultures.

$^{125}$I-TGF-$β_1$-affinity Labeling of Cell-surface TGF-β Receptors in Mink Lung Epithelial Cells Mink lung epithelial cells grown on 60-mm Petri dishes were incubated with 0.1 lnM $^{125}$I-TGF-$β_1$ in the presence of various concentrations of $P^{25}$ (41–65) or $β_3^{25}$ (41–65) in binding buffer. After 2.5 hr at 0° C., $^{125}$I-TGF-$β_1$-affinity labeling was carried out in the presence of DSS as described previously. The $^{125}$I-TGF-$β_1$ affinity-labeled TGF-β receptors were analyzed by 5% SDS-polyacrylamide gel electrophoresis under reducing conditions and autoradiography.

[Methyl-$^3$H]thymidine Incorporation

Mink lung epithelial cells grown on 24-well clustered dishes were incubated with various concentrations of TGF-$β_1$ in the presence and absence of $β_1^{25}$ (41–65) or with various concentrations of $β_1^{25}$ (41–65)-CA, and $β_1^{25}$ (41–65)-BSA in DMEM containing 0.1% fetal calf serum. After 16 hr at 37° C., the cells were pulsed with 1 μCi/ml of [methyl-$^3$H]thymidine for 4 hr. The cells were then washed twice with 1 ml of 10% trichloroacetic acid and once with 0.5 ml of ethanol:ether (2:1, v/v). The cells were then dissolved in 0.4 ml of 0.2N NaOH and counted with a liquid scintillation counter.

RNA Analysis

Mink lung epithelial cells were grown overnight in 12-well clustered dishes in DMEM containing 10% fetal calf serum. The medium was then changed to DMEM containing 0.1% fetal calf serum and the cells were incubated with 0.25 and 2.5 pM TGF-$β_1$ in the presence of various concentrations of $β_1^{25}$ (41–65) for 2.5 hr. Total cellular RNA was extracted using RNAzol B (Tel-Test Inc.) according to the manufacturer's protocol. RNA was electrophoresed in 1.2% agarose-formaldehyde gel and transferred to Duralon-UV membranes using 10×SCC. The membranes were probed at 42° C. with a random-primed, radiolabeled one kb fragment from the Hind III and NeoI digests of PAI-1 cDNA and glyceraldehyde-3-phosphate dehydrogenase (G3PDH) cDNA. The blots were washed with 0.1×SCC containing 0.1% SDS at room temperature.

References

1. Derynck, R., Jarrett, J. A., Chen, E. Y., Eaton, D. H., Bell, J. R., Assoian, R. K., Roberts, A. B., Sporn, M. B., and Goeddel, D. V. (1985) Nature 316, 701–705.
2. Laiho, M., Weis, F. M. B., and Massague, J. (1990) J. Biol. Chem. 265:18518–18524.
3. Madison, L., Webb, N. R., Rose, T. M., Marquardt, H., Ikeda, T., Twardzik, D., Seyedin, S., and Purchio, A. F. (1988) DNA and Cell Biol. 7:18.
4. Schlunegger, M. P., and Grutter, M. G. (1992) Nature 353:430–434.
5. Hinck, A. P., Archer, S. J., Qian, S. W., Roberts, A. B., Sporn, M. B., Weatherbee, J. A., Tsang, M. L.-S., Lucas, R., Zhang, B.-L., Wenker, J., and Torchia, D. A. (1996) Biochem. 35:8517–8534.
6. Liu, Q., Huang, S. S., and Huang, J. S. (1997) J. Biol. Chem, in press.
7. O'Grady, P., Kuo, M.-D., Baldassare, J. J., Huang, S. S., and Huang, J. S. (1991) J. Biol. Chem. 288:8583–8589.

What I claim my invention is:

1. A peptide of 10–25 amino acids comprising amino acids 49–58 of a TGF-$\beta_2$, wherein the peptide is capable of inhibiting specific binding of a TGF-$\beta$ to a TGF-$\beta$ receptor on a cell.

2. The peptide of claim 1, wherein the cell is a mink lung epithelial cell.

3. The peptide of claim 1, comprising SEQ ID NO:8.

4. The peptide of claim 3, consisting of SEQ ID NO:8.

5. The peptide of claim 3, consisting of SEQ ID NO:5.

6. A peptide of at least 10 amino acids comprising amino acids 49–58 of a TGF-$\beta_2$, wherein the peptide is capable of blocking TGF-$\beta$-induced growth inhibition of a cell.

7. The peptide of claim 6, wherein the cell is a mink lung epithelial cell.

8. The peptide of claim 6, comprising SEQ ID NO:8.

9. The peptide of claim 8, comprising SEQ ID NO:5.

10. A peptide of at least 25 amino acids comprising amino acids 41–65 of a TGF-$\beta_3$, wherein the peptide is capable of blocking TGF-$\beta$-induced growth inhibition of a cell.

11. The peptide of claim 10, wherein the cell is a mink lung epithelial cell.

12. The peptide of claim 10, comprising SEQ ID NO:6.

13. A peptide of at least 25 amino acids comprising amino acids 41–65 of a TGF-$\beta_1$, wherein the peptide is capable of inhibiting specific binding of a TGF-$\beta$ to a TGF-$\beta$ receptor on a cell.

14. The peptide of claim 13, comprising SEQ ID NO:4.

15. The peptide of claim 13, wherein the cell is a mink lung epithelial cell.

16. A peptide of at least 25 amino acids comprising amino acids 41–65 of a TGF-$\beta_1$, wherein the peptide is capable of blocking TGF-$\beta$-induced growth inhibition of a cell.

17. The peptide of claim 16, comprising SEQ ID NO:4.

18. The peptide of claim 16, wherein the cell is a mink lung epithelial cell.

19. A method of inhibiting specific binding of a TGF-$\beta$ to a TGF-$\beta$ receptor on a cell comprising contacting the cell with a peptide of 10–25 amino acids, wherein (a) the peptide comprises amino acids 49–58 of a TGF-$\beta_1$ or amino acids 49–58 of a TGF-$\beta_2$, and (b) the peptide inhibits the specific binding of a TGF-$\beta$ to a TGF-$\beta$ receptor on said cell.

20. The method of claim 19, wherein the cell is a mink lung epithelial cell.

21. The method of claim 19, wherein the peptide comprises SEQ ID NO:7 or SEQ ID NO:8.

22. The method of claim 21, wherein the peptide comprises SEQ ID NO:7.

23. The method of claim 22, wherein the peptide consists of SEQ ID NO:7.

24. The method of claim 22, wherein the peptide consists of SEQ ID NO:4.

25. The method of claim 21, wherein the peptide comprises SEQ ID NO:8.

26. The peptide of claim 25, wherein the peptide consists of SEQ ID NO:8.

27. The method of claim 25, wherein the peptide consists of SEQ ID NO:5.

28. A method of blocking TGF-$\beta$-induced growth inhibition of a cell comprising contacting the cell with a peptide of at least 10 amino acids, wherein (a) the peptide comprises amino acids 49–58 of a TGF-$\beta_2$ or consists of amino acids 49–58 of a TGF-$\beta_1$, and (b) the peptide blocks TGF-$\beta$-induced growth inhibition of said cell.

29. The method of claim 28, wherein the cell is a mink lung epithelial cell.

30. The method of claim 28, wherein the peptide consists of SEQ ID NO:7.

31. The method of claim 28, wherein the peptide comprises SEQ ID NO:8.

32. The method of claim 31, wherein the peptide comprises SEQ ID NO:5.

33. A method of blocking TGF-β-induced growth inhibition of a cell comprising contacting the cell with a peptide of at least 25 amino acids, wherein (a) the peptide comprises amino acids 41–65 of a TGF-$\beta_1$ or amino acids 41–65 of a TGF-$\beta_3$, and
(b) the peptide blocks TGF-β-induced growth inhibition of said cell.

34. The method of claim 33, wherein the cell is a mink lung epithelial cell.

35. The method of claim 34, wherein the peptide comprises SEQ ID NO:4.

36. The method of claim 33, wherein the peptide comprises SEQ ID NO:6.

* * * * *